United States Patent

Knifton et al.

[11] Patent Number: 5,183,947
[45] Date of Patent: Feb. 2, 1993

[54] ONE STEP SYNTHESIS OF METHYL T-BUTYL ETHER FROM T-BUTANOL USING FLUOROPHOSPHORIC ACID-MODIFIED CLAY CATALYSTS

[75] Inventors: John F. Knifton, Austin; John R. Sanderson, Leander, both of Tex.

[73] Assignee: Texaco Chemical Company, White Plains, N.Y.

[21] Appl. No.: 900,999

[22] Filed: Jun. 19, 1992

[51] Int. Cl.$^5$ .............................................. C07C 41/09
[52] U.S. Cl. .................................... 568/698; 568/697
[58] Field of Search ............................... 568/697, 698

[56] References Cited

U.S. PATENT DOCUMENTS

| | | | |
|---|---|---|---|
| 2,282,469 | 5/1942 | Frolich | 568/698 |
| 4,822,921 | 4/1989 | Knifton et al. | 568/698 |
| 4,827,048 | 5/1989 | Knifton | 568/698 |
| 4,918,244 | 4/1990 | Nelson et al. | 568/698 |
| 4,925,989 | 5/1990 | Hagan et al. | 568/698 |
| 5,059,725 | 10/1991 | Knifton et al. | 568/698 |
| 5,081,318 | 1/1992 | Knifton | 568/698 |
| 5,099,072 | 3/1992 | Knifton | 568/698 |

OTHER PUBLICATIONS

Adams et al., "Clays and Clay Minerals", vol. 34, No. 5, (1986), pp. 597, 603.

Primary Examiner—Werren B. Lone
Attorney, Agent, or Firm—Jack H. Park; Kenneth R. Priem; Cynthia L. Kendrick

[57] ABSTRACT

A method is disclosed wherein t-butanol is reacted with methanol in a reaction zone in one step to provide methyl tert-butyl ether and the improvement of accomplishing the reaction which comprises:

a. Using a catalyst comprising a montmorillonite clay treated with a fluorophosphoric acid,
b. Continuously contacting said t-butanol and methanol in a molar amount of about 0.1 to 10 moles of methanol per mole of t-butanol with said catalyst at a temperature of about 20° C. to about 250° C. and a pressure of about atmospheric to about 1000 psig to obtain the methyl tert-butyl ether product.

7 Claims, No Drawings

ONE STEP SYNTHESIS OF METHYL T-BUTYL ETHER FROM T-BUTANOL USING FLUOROPHOSPHORIC ACID-MODIFIED CLAY CATALYSTS

CROSS-REFERENCE

The application is related to U.S. Pat. Nos. 4,827,048; 4,822,921; 5,059,725 and 5,081,318 and to copending application Ser. Nos. 07/796,987 and 07/783,015, held allowable, and to U.S. application Ser. Nos. 07/494,280; 07/494,281; 07/724,071, and 07/745,777.

This invention concerns an improved process for preparing methyl tertiary-butyl ether (MTBE) by the reaction of tertiary-butanol and methanol in the presence of a catalyst comprising a fluorophosphoric acid-modified montmorillonite clay catalyst. MTBE has been generated in up to 40% concentration in the crude product. This catalyst demonstrates improved yields of MTBE product compared with unmodified montmorillonite clay. Another desirable feature is that the product mix separates into an isobutylene-MTBE product-rich phase and a heavier aqueous methanol phase at operating temperatures of 160° C. or greater.

BACKGROUND OF THE INVENTION

It is known to those ski)led in the art that ethers, including unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Methyl tert-butyl ether is finding increasing use as a blending component in high octane gasoline as the current gasoline additives based on lead and manganese are phased out. Currently all commercial processes for the manufacture of methyl tert-butyl ether are based upon the liquid-phase reaction of isobutylene and methanol (Eq. 1), catalyzed by a cationic ion-exchange resin (see, for example: Hydrocarbon Processing, Oct. 1984, p. 63; Oil and Gas J., Jan. 1, 1979, p. 76; Chem. Economics Handbook-SRI, Sept. 1986, p. 543-7051P). The cationic ion-exchange resins used in MTBE synthesis normally have the sulphonic acid functionality (see: J. Tejero, J. Mol. Catal., 42 (1987) 257; C. Subramamam et al., Can. J. Chem. Eng., 65 (1987) 6l3).

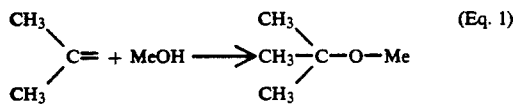

(Eq. 1)

With the expanding use of MTBE as an acceptable gasoline additive, a growing problem is the availability of raw materials. Historically, the critical raw material is isobutylene (Oil and Gas J., Jun. 8, 1987, p. 55). It would be advantageous, therefore, to have a process to make MTBE that does not require isobutylene as a building block. It would be advantageous to have an efficient process for making MTBE by reaction of methanol with tertiary-butyl alcohol, since t-butanol (TBA) is readily available commercially through isobutane oxidation.

In U.S. Pat. No. 4,144,138 (1979) to Rao et al., there is disclosed a method for recovering methyl tertiary-butyl ether from etherification reaction effluent by azeotropic distillation to recover methanol-ether azeotrope overhead which is water-washed to give pure ether raffinate plus ether-methanol bottoms, the latter being azeotropically distilled to yield ether-methanol overhead which is recycled to water washing.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl. Vses Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process. It is also pointed out that, although a plant for etherification over cation exchangers does not present any major problems, considerations include the fact that recycling large amounts of tert-butyl alcohol and methanol, as well as isobutylene, causes the scheme to be somewhat more expensive. Also, the progress of the reaction over cation exchangers is usually complicated by various adsorption and diffusion factors, by swelling phenomena, and by the variable distribution of the components between the solution and ion-exchanger phase. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

In U.S. Pat. No. 2,282,469 to Frolich there is disclosed a process for preparing methyl tertiary-butyl ether over a catalyst comprising Kieselguhr impregnated with phosphoric acid at a temperature of about 175° F. to 350° F.

In an article titled "Catalysis: Selective Developments", Chem. Systems Report 84-3, 239-249, at section 3.4320, the unusual properties of smectite clays which make them of interest as catalysts are discussed. These compositions are layered and exhibit a 2:1 relationship between tetrahedral and octahedral sites. In addition the combination of cation exchange, intercalation and the fact that the distance between the layers can be adjusted provide interesting possibilities.

There is a discussion of clay mineral catalysts, including "acid" montmorillonite clay catalysts in "Progress in Inorganic Chemistry", Vol. 35, p. 41 (1987). The process of pillaring this type of catalyst is discussed. Pillaring can convert a clay lamellar solid into a more heat resistant two dimensional zeolite material.

G. B. Patent No. 2,179,563 (1987) discloses the use of modified layered clay catalysts in reactions capable of catalysis by protons. Of particular interest in this invention were the three-layer sheet types, such as smectites, micas and vermiculites composed of successive layers of tetrahedral silica, octahedral alumina and tetrahedral silica which can exhibit swelling properties.

U.S. Pat. No. 4,590,294 (1986) discloses a process for the production of an ester comprising reacting an olefin from the group consisting of ethylene, hex-1-ene, hept-1-ene, oct-1-ene, 4-methylpent-1-ene, hex-2-ene, 1,5-hexadiene and cyclohexene with a carboxylic acid using as a catalyst component a hydrogen ion-exchanged layered clay. This reference would not seem to suggest a method for simultaneous dehydration of tert-butanol to isobutylene and the reaction with methanol to produce MTBE.

In U.S. Pat. No. 4,822,921 (1989), listed in the cross-references, there is disclosed a method for producing MTBE by reacting tertiary-butyl alcohol and methanol in the presence of a catalyst comprising an inert support, such as titania, having a phosphoric acid impregnated thereon.

U.S. Pat. No. 4,827,048 (1989), also referred to in the cross-references, discloses a method for producing MTBE by reacting tertiary-butyl alcohol and methanol in the presence of a catalyst comprising a heteropoly acid such as 12-tungstophosphoric acid or 12-molybdophosphoric acid on an inert support, such as titania.

In copending U.S. patent application Ser. No. 07/494,281, there is disclosed a method for preparing methyl tertiary-butyl ether by reacting t-butanol and methanol in the presence of a catalyst comprising a super-acid alumina or a faujasite-type zeolite.

Copending U.S. patent application Ser. No. 07/494,280 discloses the reaction of t-butanol and methanol in the presence of acidic montmorillonite clay catalysts having certain identifiable physical parameters, such as surface area, acidity range and moisture content.

In U.S. Pat. No. 5,081,318 (1992), there is described a one-step method for the synthesis of MTBE from t-butanol using a fluorosulfonic acid-modified zeolite catalyst.

In U.S. Pat. No. 5,059,725 (1991), a one-step synthesis for MTBE is disclosed wherein t-butanol and methanol are reacted over a catalyst comprising ammonium sulfate or sulfuric acid deposited upon a Group IV oxide.

In Ser. No. 07/724,071 a fluorocarbon sulfuric acid polymer on an inert support is disclosed for use as a catalyst for producing MTBE. And, in Ser. No. 07/745,777 there is disclosed the use of a hydrogen fluoride-modified zeolite catalyst for the production of MTBE.

Ser. No. 07/796,987 and 07/783,015, both allowed, claim the one step synthesis of MTBE using a multimetal-modified clay catalyst or a fluorosulfonic acid-modified clay catalyst, respectively.

In Ser. No. 07/878,121 there is described a haloacid-modified montmorillonite clay catalyst for producing MTBE from t-butanol and methanol.

With the current interest in the production of MTBE as a blending component in high octane gasoline, the identification of novel catalysts which provide substantial yields is important in the art. If a catalyst provides substantial yields, permits the production of MTBE in one step and incorporates the added feature of phase separation of the product above a certain temperature, such a catalyst represents a substantial advance in the art.

SUMMARY OF THE INVENTION

In accordance with certain of its aspects, the novel method of this invention for preparing methyl tert-butyl ether from tertiary-butyl alcohol (t-butanol) and methanol in one-step comprises reacting tertiary-butyl alcohol and methanol in the presence of a catalyst comprising a fluorophosphoric acid-modified montmorillonite clay at an elevated temperature and moderate pressure. Examples demonstrate particularly the effectiveness of montmorillonite clays modified with difluorophosphoric acid.

DESCRIPTION OF THE INVENTION

Preparation of the product of this invention may be carried out typically by reacting tertiary-butyl alcohol and methanol in the presence of an etherification catalyst. The etherification is carried out in one step and the catalyst comprises a fluorophosphoric acid-modified montmorillonite clay.

The reaction can be represented by the following:

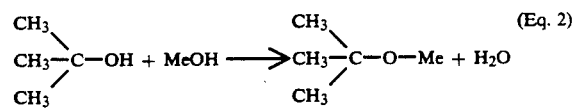

Generally the methanol and t-butanol coreactants may be mixed in any proportion in order to generate the desired methyl t-butyl ether, but preferably the molar ratio of methanol to t-butanol in the feed mixture should be between 10:1 and 1:10, if the yield of desired MTBE is to be maximized. In order to achieve maximum selectivity to MTBE, and optimum conversion per pass, an excess of methanol in the liquid feed is desirable. The most preferred methanol-to-tertiary-butanol molar ratio is from 1:1 to 5:1. Optionally, said t-butanol plus methanol feed mixtures may be crude feedstocks containing other components, including water, ketones such as acetone, other alcohols such as 2-propanol, peroxides such as di-t-butyl peroxide, t-butyl hydroperoxide and allyl t-butyl peroxide, esters such as t-butyl formate, as well as methyl t-butyl ether product.

In certain circumstances, it may be particularly desirable that the TBA conversion be high enough (e.g. >40% per pass), such that the crude product mix phase separates into an isobutylene-MTBE product-rich phase and a heavier aqueous methanol phase. Preferably such a product phase separation would be achieved at as low an etherification temperature as possible, but particularly in the range 160°-200° C.

The same process may also be applied to the preparation of other alkyl tertiary alkyl ethers. For example, said process may be applied to the reaction of a $C_1$-$C_6$ primary alcohol such as methanol, ethanol, n-propanol and n-hexanol with a $C_4$-$C_{10}$ tertiary alcohol such as, for example, tertiary-butanol and tertiary amyl alcohol. Reaction of methanol with tertiary amyl alcohol (2-methyl-2-butanol) would then yield methyl tertiary amyl ether (TAME). Alternatively a mixture of alcohols, e.g., a mixture of $C_1$-$C_5$ alcohols, could be reacted to give a mixture of alkyl tert-alkyl ethers.

Good results were realized using certain phosphoric acid and fluorophosphoric acid-modified clays as catalysts for the reaction in Eq. 2, particularly difluorophosphoric acid-modified montmorillonite clays.

The clays used to form this catalyst are silica-alumina clays. Chemically, clays are composed primarily of silicon, aluminum and oxygen, with minor amounts of magnesium and iron in some cases. Variations in the ratios of these constituents, and their crystal lattice configurations, result in some fifty separate clays, each with its own characteristic properties.

Particularly effective in reaction (Eq. 2) are smectite clays. Smectite clays are discussed in the article cited in Chem. Systems Report, 84-3. These clays have small particle size and unusual intercalation properties which afford them high surface area. They are alumino silicates with a unique structure that permits modifications which provide useful catalysts. They comprise layered sheets of octahedral sites between sheets of tetrahedral sites, where the distance between the layers can be adjusted by swelling. This layering is illustrated in an article by F. Figueras, Catal. Rev.-Sci. Eng., 30, 457 (1988). What renders the smectites of interest among the clay minerals is the combination of cation exchange, intercalation, and the fact that the distance between the layers can be adjusted by treatment with the appropriate solvent etc.

The three layered sheet types include montmorillonite, vermiculite and some brittle mica. The idealized basic structure of clays of this type is that of a pyrophyllite which has the basic formula $Si_8Al_4O_{10}(OH)_4$.

A general representation of the montmorillonite structure is:

$$M_{x/n}{}^{n+} \cdot yH_2O(Al_{4-x}Mg_x)(Si_8)O_{20}(OH)_4$$

Where:
M represents the interlamellar (balancing cations), normally sodium or lithium and x, y and n are integers. The value of x depends on the origin of the mineral.

Said montmorillonite clays are preferably treated with a fluorophosphoric acid as demonstrated in Examples 1 through 4. Fluorophosphoric acids useful for modifying the montmorillonite clays are selected from the group consisting of monofluorophosphoric acid $[O=P(OH)_2F]$, difluorophosphoric acid $[O=P(OH)F_2]$ and hexafluorophosphoric acid (HPF6), in addition to phosphoric acid ($H_3PO_4$). 5 Good results were observed using difluorophosphoric acid, as demonstrated in Example 1 and 2 of Table I. Examples 3 and 4 demonstrate good results using fluorophosphoric acid and phosphoric acid.

The montmorillonite clays to be modified may be in the form of powders, pellets, granules, spheres, shapes and extrudates. The examples described herein demonstrate certain advantages using powders. An example of a commercially-available, neutral, montmorillonite clay which can be treated with a fluorophosphoric acid is Engelhard Grade 2C powder, having a typical moisture content of 16% and a particle size of >100 mesh.

Preparation of the fluorophosphoric acid-modified clay is accomplished by adding a solution of the fluorophosphoric acid in distilled water, or in an organic solvent, such as acetone, to the neutral clay which is preferably in powdered form. The mixture is then stirred for from about one to 48 hours, under a nitrogen blanket, washed with distilled water and/or an appropriate organic solvent, and dried in vacuo at from about 20° to 100° C., followed by 20° to 300° C. Said fluorophosphoric acid-modified clays generally have titratable acidities up to 1 meq/g or higher.

It has been discovered that fluorophosphoric acid-modified clays possess a number of improved properties for the production of MTBE. The performance of representative fluorophosphoric acid-modified clays in MTBE synthesis from t-butanol and methanol in one-step (Eq. 2) is illustrated by the accompanying examples.

The reaction may be carried out in either a stirred slurry reactor or in a fixed bed continuous flow reactor. The catalyst concentration should be sufficient to provide the desired catalytic effect.

Etherification can generally be conducted at temperatures from 20° to 250° C.; the preferred range is 80° to 200° C. As mentioned, at temperature of 160° C. or greater two phases are observed in the product. The total operating pressure may be from 0 to 1000 psig, or higher. The preferred pressure range is 50 to 500 psig.

Typically, MTBE is generated continuously in up to about 40 wt% concentration in the crude liquid product at total liquid hourly space velocities (LHSV) of up to 5 or higher and relatively mild conditions, where:

$$LHSV = \frac{\text{Volume Of Total Liquid Feed Run Through The Reactor Per Hour}}{\text{Volume of Catalyst In Reactor}}$$

Conversions of t-butanol (TBA, wt%) are estimated in the following examples using the equation:

$$\frac{(\text{Wt \% Conc. of } TBA \text{ in Feed} - \text{Wt \% Conc. of } TBA \text{ in Product})}{\text{Wt \% Conc. of } TBA \text{ in Feed}} \times 100$$

Selectivities of methyl t-butyl ether (MTBE, mole %) and isobutylene ($C_4H_8$, mole%) are estimated from:

$$\frac{\text{Moles of } MTBE \text{ (or } C_4H_8\text{) in Product}}{\text{moles of } TBA \text{ converted}} \times 100$$

The examples which follow illustrate the one-step synthesis of MTBE from TBA and MeOH (Eq. 2) using fluorophosphoric acid-modified clays particularly in powdered form. The examples are only intended as a means of illustration and it is understood the invention is not meant to be limited thereby.

The following can be noted:
1) Comparing etherification data in Table I and Example 2 using the difluorophosphoric acid-modified montmorillonite clay, prepared by the method of Example 1, with data for the untreated clay (comparative Example A and Table IV) it may be noted that:
a) The TBA conversion levels with the difluorophosphoric acid-treated clay of example 2 at all operating temperatures are measurably higher than for the untreated clay.
b) Only the difluorophosphoric acid clay of Example 2 achieves phase separation into an isobutylene MTBE product rich phase and a heavier aqueous methanol phase at a temperature of 160°-180° C.

2) Excellent etherification catalyst activities are realized in Example 3 and Table II using a fluorophosphoric acid-modified clay and in Example 4 and Table III when employing a phosphoric acid-modified clay.

EXAMPLE 1

This example illustrates the preparation of a difluorophosphoric acid-modified montmorillonite clay.

To 100g of neutral montmorillonite clay (Engelhard Grade F2C, powder) was added a solution of difluorophosphoric acid (10.0 g) in distilled water (100 cc). The mixture was stirred for 24 hours at room temperature, under nitrogen, the solids filtered off and then first washed with distilled water, followed by drying in vacuo at 40° C. for 4 hours and 150° C., overnight.

The recovered white powder was found to comprise by analysis.
Phosphorous Content, 0.02%
Water Content, 1.3%
Acidity, 0.07 meq/g

EXAMPLE 2

This example illustrates the production of methyl t-butyl ether from t-butanol and methanol using a difluorophosphoric acid-modified montmorillonite clay.

Synthesis was conducted in a tubular reactor (⅜" i.d., 12" long), constructed of 316ss, operated upflow and mounted in a furnace controllable to ±1.0° C. and fitted with pumps allowing flow control to <±1 cc/hr. The reactor was also fitted with a pressure regulating device and equipment for monitoring temperature, pressure and flow rate.

The reactor was charged at the beginning of the experiment with 25 cc of difluorophosphoric acid-modified clay powder, prepared by the method of Example 1. A screen of glass wool was placed at the top and bottom of the reactor to ensure the catalyst would remain in the middle portion.

The catalyst bed was treated with a methanol/t-butanol (1.1:1 molar mix) upflow, at a flow rate of 50 cc/hr, while the reactor was held at 120° C., with a total pressure of 300 psi. Samples of crude product effluent were collected periodically on-stream, in 316ss bombs and analyzed by glc and gc-ir.

Typically analyses data for samples taken under these conditions are summarized in Table I. Performance at a series of other temperatures (140°, 160° and 180° C.) was determined using the same procedure. These results are also given in Table I.

Of note, conversion levels and isobutylene/MTBE selectivities at 120° C., 140° C. and 160° C. are as follows:

| Sample | Operating Temp (°C.) | tBA Conv (%) | Molar Selectivity (%) C$_4$H$_8$ | MTBE |
|---|---|---|---|---|
| 1 | 120 | 46 | 25 | 73 |
| 3 | 140 | 64 | 31 | 66 |
| 5 | 160 | 86 | a | a |

[a] Not Determined

TABLE I

MTBE/ISOBUTYLENE SYNTHESIS

| Ex. | Catalyst | MeOH/tBA Molar Ratio | Feed Rate (cc/hr) | Temp. (°C.) | Time On Stream (Days) | Sample | H$_2$O | MeOH | C$_4$H$_8$ | tBA | MTBE |
|---|---|---|---|---|---|---|---|---|---|---|---|
| 2 | Ex. 1[a] | 1.1:1 | 50 | | | FS-1 | 0.1 | 31.0 | | 68.6 | |
| | | | | 120 | 1 | →1 | 7.9 | 21.7 | 5.8 | 37.3 | 27.1 |
| | | | | | | 2 | 7.7 | 22.2 | 5.6 | 38.4 | 25.8 |
| | | | | 140 | 2 | →3 | 11.1 | 19.3 | 10.1 | 24.9 | 34.4 |
| | | | | | | 4 | 11.1 | 19.7 | 9.4 | 26.1 | 33.4 |
| | | | | 160 | 3 | →5 | 6.2 | 16.2 | 33.8 | 10.3 | 33.2 |
| | | | | | | | 35.0 | 41.4 | 4.4 | 8.8 | 9.3 |
| | | | | | | 6 | 7.4 | 17.7 | 29.5 | 12.0 | 33.2 |
| | | | | | | | 36.4 | 39.8 | 4.0 | 9.2 | 9.7 |
| | | | | 180 | 4 | 7 | 2.9 | 11.9 | 52.3 | 6.8 | 25.9 |
| | | | | | | | 32.4 | 46.3 | 4.9 | 8.5 | 7.5 |
| | | | | | | 8 | 3.4 | 12.7 | 50.4 | 7.2 | 26.0 |
| | | | | | | [b] | 31.5 | 46.0 | 5.7 | 8.7 | 7.7 |

[a] Difluorophosphoric Acid on Clay 2C, Powder
[b] Recovered Catalyst: H$_2$O, 3.1%; Acidity, 0.08 meq/g

EXAMPLES 3 AND 4

In these examples, following the procedures of Example 2, a fluorosphosphoric acid-modified montmorillonite clay powder and a granular phosphoric acid-modified clay were each evaluated for the cosynthesis of MTBE plus isobutylene from t-butanol/methanol (1:1.1 mixtures).

The fluorophosphoric acid-on-montmorillonite clay was prepared according to the method of Example 1 and had the following composition:

Phosphorous Content, 0.03%
Water Content, 1.2%
Acidity, 0.06 meq/g

The phosphoric acid-on-granular clay had the following composition:

Phosphorous Content, 2.1%
Water Content, 20.5%
Acidity, 0.18 meq/g

The results for the fluorophosphoric acid-modified clay are given in Table II and the MTBE/isobutylene data for the phosphoric acid-modified clay are summarized in Table III.

TABLE II

MTBE/ISOBUTYLENE SYNTHESIS

| Ex. | Catalyst | MeOH/tBA Molar Ratio | Feed Rate (cc/hr) | Temp. (°C.) | Time On Stream (Days) | Sample | H$_2$O | MeOH | C$_4$H$_8$ | tBA | MTBE |
|---|---|---|---|---|---|---|---|---|---|---|---|
| 3 | P.F/Clay[a] | 6798-1.1:1 | 50 | | | FS-1 | | 31.5 | | 68.2 | |
| | | | | 120 | 1 | 1 | 11.3 | 17.8 | 7.4 | 23.7 | 39.6 |
| | | | | | | 2 | 11.2 | 17.9 | 7.6 | 23.6 | 39.5 |
| | | | | 140 | 2 | 3 | 12.2 | 19.1 | 12.4 | 19.8 | 36.2 |
| | | | | | | 4 | 12.2 | 19.1 | 12.2 | 20.1 | 36.2 |
| | | | | | | [b] | | | | | |

TABLE II-continued

| | | | | | Time On | | \multicolumn{5}{c}{MTBE/ISOBUTYLENE SYNTHESIS} |
| | | MeOH/tBA Molar | Feed Rate | Temp. | Stream | | \multicolumn{5}{c}{Product Composition (wt %)} |
| Ex. | Catalyst | Ratio | (cc/hr) | (°C.) | (Days) | Sample | H₂O | MeOH | C₄H₈ | tBA | MTBE |

| Ex. | Catalyst | MeOH/tBA Molar Ratio | Feed Rate (cc/hr) | Temp. (°C.) | Time On Stream (Days) | Sample | H₂O | MeOH | C₄H₈ | tBA | MTBE |
|---|---|---|---|---|---|---|---|---|---|---|---|
| | | | | 160 | 3 | 5 | 36.4 | 42.9 | 3.6 | 7.9 | 8.7 |
| | | | | | | 6 | 4.1 | 14.0 | 41.1 | 8.1 | 32.3 |
| | | | | | | | 36.7 | 42.4 | 3.6 | 8.0 | 8.9 |
| | | | | 180 | 4 | 7 | 2.0 | 10.3 | 59.1 | 4.9 | 23.4 |
| | | | | | | | 32.8 | 48.2 | 4.6 | 7.3 | 6.6 |
| | | | | | | 8 | 2.4 | 11.3 | 56.4 | 5.5 | 24.0 |
| | | | | | | | 32.4 | 47.3 | 4.9 | 7.6 | 7.2 |

[a]Fluorophosphoric Acid on Clay 2C, Powder
[b]Insufficient Sample for Analysis

TABLE III

MTBE/ISOBUTYLENE SYNTHESIS

| Ex. | Catalyst | MeOH/tBA Molar Ratio | Feed Rate (cc/hr) | Temp. (°C.) | Time On Stream (Days) | Sample | H₂O | MeOH | C₄H₈ | tBA | MTBE |
|---|---|---|---|---|---|---|---|---|---|---|---|
| 4 | P/Clay[a] | 1.1:1 | 50 | | | FS-1 | | | | 68.9 | |
| | | | | 120 | 1 | 1 | 10.9 | 18.6 | 7.8 | 27.5 | 36.0 |
| | | | | | | 2 | 9.8 | 18.8 | 7.8 | 28.0 | 35.4 |
| | | | | 140 | 2 | 3 | 11.5 | 18.3 | 12.8 | 19.9 | 37.3 |
| | | | | | | 4 | 11.8 | 18.2 | 12.9 | 19.8 | 37.1 |
| | | | | 160 | 3 | 5 | 8.3 | 17.1 | 29.2 | 10.4 | 34.7 |
| | | | | | | | 41.0 | 36.6 | 3.1 | 8.5 | 10.5 |
| | | | | | | 6 | 9.3 | 17.8 | 28.0 | 10.6 | 34.1 |
| | | | | | | | 41.6 | 36.2 | 3.0 | 8.6 | 10.4 |
| | | | | 180 | 4 | 7 | 8.4 | 18.2 | 52.3 | 4.3 | 16.6 |
| | | | | | | | 33.4 | 49.1 | 4.8 | 6.6 | 5.8 |
| | | | | | | 8 | 15.6 | 27.3 | 38.3 | 5.0 | 13.5 |
| | | | | | | | 33.9 | 48.3 | 4.7 | 6.6 | 6.0 |

[a]Phosphoric Acid on Clay

COMPARATIVE EXAMPLE A

This comparative example illustrates the performance of unmodified montmorillonite clay in the production of methyl t-butyl ether from t-butanol and methanol.

Using the equipment and procedures of Example 2, 25 cc of untreated montmorillonite clay (Engelhard Grade 2C clay powder) was charged to the reactor system and performance was monitored over a series of temperatures (120°, 140°, 160° and 180° C.). The tBA/MeOH (1:1.1) feed rate was maintained at 50 cc/hr. The results are summarized in Table IV.

Calculated tBA conversion and C₄H₈/MTBE selectivities for Samples 2 and 6 are as follows:

| Sample | Operating Temp (°C.) | tBA Conv (%) | Molar Selectivity (%) C₄H₈ | MTBE |
|---|---|---|---|---|
| 2 | 120 | <1 | | |
| 6 | 160 | 25 | 34 | 63 |

TABLE IV

MTBE/ISOBUTYLENE SYNTHESIS

| Ex. | Catalyst | MeOH/tBA Molar Ratio | Feed Rate (cc/hr) | Temp. (°C.) | Time On Stream (Days) | Sample | H₂O | MeOH | C₄H₈ | tBA | MTBE |
|---|---|---|---|---|---|---|---|---|---|---|---|
| A | Clay 2C[a] | 1.1 | 50 | | | FS-1 | | 31.4 | | 67.9 | |
| | | | " | 120 | 1 | 1 | 0.1 | 31.4 | 0.2 | 67.7 | 0.4 |
| | | | | | | →2 | 0.2 | 31.3 | 0.3 | 67.4 | 0.6 |
| | | | " | 140 | 2 | 3 | 1.3 | 30.7 | 1.0 | 63.9 | 2.9 |
| | | | | | | 4 | 0.8 | 30.8 | 0.9 | 64.7 | 2.5 |
| | | | " | 160 | 3 | 5 | 3.0 | 28.2 | 3.5 | 55.5 | 9.5 |
| | | | | | | →6 | 4.4 | 27.3 | 4.5 | 50.6 | 12.9 |
| | | | " | 180 | 4 | 7 | 10.0 | 22.1 | 12.8 | 26.5 | 28.2 |
| | | | | | | 8 | 9.9 | 22.4 | 12.6 | 26.9 | 27.9 |

[a]Engelhard Clay Grade 2C

What is claimed is:

1. In a method wherein t-butanol is reacted with methanol in one step in the presence of a catalyst to provide methyl tert-butyl ether, the improvement comprising using as a catalyst a montmorillonite clay modified with an acid from the group consisting of a fluorophosphoric acid or phosphoric acid and continuously contacting said t-butanol and methanol in a molar amount of about 0.1 to 10 moles of methanol per mole of t-butanol with said catalyst at a temperature of about 20° C. to about 250° C. and a pressure of about atmospheric to about 1000 psig to obtain methyl tert-butyl ether product.

2. The method of claim 1 wherein the fluorophosphoric acid is selected from the group consisting of monofluorophosphoric, difluorophosphoric and hexafluorophosphoric acid.

3. The method of claim 1 wherein the fluorophosphoric acid is difluorophosphoric acid.

4. The method of claim 1 wherein the temperature is from about 80° C. to about 200° C.

5. The method of claim 1 wherein the operating temperature is in the range 160° to 200° C. and the product comprises a two-phase mix of an isobutylene-MTBE product-rich phase and a heavier aqueous methanol-rich phase.

6. The method of claim 1 wherein said montmorillonite clay has the structure:

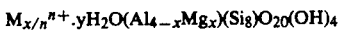

$$M_{x/n}{}^{n+} \cdot yH_2O(Al_{4-x}Mg_x)(Si_8)O_{20}(OH)_4$$

Where: M represents the interlamellar balancing cations, normally sodium or lithium and x, y and n are integers.

7. The method of claim 2 wherein the fluorophosphoric acid-treated clay has an acidity in the range 0–1 meq/g.

* * * * *